(12) United States Patent
O'Neill et al.

(10) Patent No.: US 6,630,105 B1
(45) Date of Patent: Oct. 7, 2003

(54) METHOD AND APPARATUS FOR THE GAS PHASE DECONTAMINATION OF CHEMICAL AND BIOLOGICAL AGENTS

(75) Inventors: Hugh J. O'Neill, Oak Forest, IL (US); Kenneth L. Brubaker, Bolingbrook, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 41 days.

(21) Appl. No.: 09/675,898

(22) Filed: Sep. 27, 2000

(51) Int. Cl.⁷ .................. A61L 2/00; B01D 53/22; B01D 39/00; F26B 19/00; B08B 3/12
(52) U.S. Cl. ............... 422/24; 422/121; 422/186.03; 422/186.05; 422/186.07; 422/305; 95/47; 95/52; 95/54; 96/10; 96/224; 438/707; 134/1; 134/1.1; 134/2; 134/22.17; 34/235; 34/275; 34/276; 588/200
(58) Field of Search ................ 204/164, 157.15, 204/157.5; 95/52, 54, 47; 96/10, 224; 438/707–709; 134/1, 1.1, 2, 22.17; 34/235, 275–276; 588/200; 422/22–24, 120–122, 186.05, 186.07, 186.03, 305

(56) References Cited

U.S. PATENT DOCUMENTS

| | | | | |
|---|---|---|---|---|
| 5,151,134 A | * | 9/1992 | Boquillon et al. | 13/1 |
| 5,656,096 A | * | 8/1997 | Van Alstyne | 134/1 |
| 5,709,754 A | * | 1/1998 | Morinville et al. | 134/1.3 |
| 6,272,768 B1 | * | 8/2001 | Danese | 34/375 |
| 6,319,328 B1 | * | 11/2001 | Greenberg et al. | 134/2 |

* cited by examiner

Primary Examiner—Robert J. Warden, Sr.
Assistant Examiner—Monzer R. Chorbaji
(74) Attorney, Agent, or Firm—Bradley W. Smith; Mark P. Dvorscak; Paul A. Gottlieb

(57) ABSTRACT

An apparatus and method for decontaminating chemical and biological agents using the reactive properties of both the single atomic oxygen and the hydroxyl radical for the decontamination of chemical and biological agents. The apparatus is self contained and portable and allows for the application of gas reactants directly at the required decontamination point. The system provides for the use of ultraviolet light of a specific spectral range to photolytically break down ozone into molecular oxygen and hydroxyl radicals where some of the molecular oxygen is in the first excited state. The excited molecular oxygen will combine with water vapor to produce two hydroxyl radicals.

9 Claims, 2 Drawing Sheets

METHOD AND APPARATUS FOR THE GAS PHASE DECONTAMINATION OF CHEMICAL AND BIOLOGICAL AGENTS

CONTRACTUAL ORIGIN OF THE INVENTION

The United States Government has rights in this invention pursuant to Contract No. W-31-109-ENG-38 between the U.S. Department of Energy and the University of Chicago.

FIELD OF THE INVENTION

This invention is an apparatus and method for providing for effective decontamination of chemical and biological agents using a gas-phase decontamination system.

BACKGROUND OF THE INVENTION

There is a critical need for rapid and effective decontamination procedures for chemical and biological agents in domestic threat scenarios in order to minimize the risk/effects of human exposure and the time periods required for the operational recovery of a targeted site. In many instances, the use of conventional aqueous decontamination agents, such as alkali, bleach, and high test hypochlorite solutions are not appropriate because they are corrosive, require bulk quantities to be available, cannot be used on sensitive electronic equipment, may cause waste management/disposal problems by violating run-off and discharge regulations if it should find its way into an urban drainage system. Further, many of the aqueous decon systems are not effective against both chemical and biological agents, cannot be effectively transported to confined areas or remote locations and could require extensive cleanup operations following their use.

The object of the present invention is to avoid the operational and logistic limitations of aqueous systems with a gas phase decon procedure which is highly reactive, effective against both chemical and biological systems, and sufficiently portable that it can be carried, back-packed or wheeled on a cart to a remote location or to a confined space without any external support systems (e.g., power, water, reagents). Although this system does generate highly reactive hydroxyl radicals, such species are short lived and do not pose a significant limitation. In reality, it is the combination of a high reactivity and short-lived specie that make this decontamination invention so attractive to utilize.

The design and configuration of this instrumentation is a small, portable, hand-carried or cart-carried or back-packed-type unit that can be readily transported into confined, remote, or isolated locations. It is ideally suited for the decontamination of sensitive equipment including: computers, electrical/electronic circuit boards, electrical switches and relays, wiring harnesses and other similar type of equipment which would be critically damaged or rendered inoperative when decontaminated with aqueous or solvent based systems. By virtue of the incorporation of a dual delivery nozzle into the configuration of this instrument, both the large outer surfaces and the limited inner surface areas of the equipment can be decontaminated. Although this instrument is directed toward the decontamination of chemical and biological agent contaminated sensitive equipment, it can equally be applied to larger surfaces (floors, ceilings, walls), as well as the sterilization of hospital equipment, surgical instruments, and other medical supplies in remote or field situations where resources are limited. Since the instrument is a gas phase decontamination technique, it is particularly applicable to sensitive equipment.

This invention is directed toward the use of the highly energetic and reactive properties of both the singlet atomic oxygen and hydroxyl radical species for the rapid and efficient decontamination of both chemical and biological agents. The application of the two reactive oxygen species $O(^1D)$ and OH toward both chemical agents and their simulants, has been the subject of prior studies, which clearly demonstrated the feasibility of this approach. In addition, these studies also suggested that this technique may be equally applicable for the decontamination of biological agents, as well. The use of atomic oxygen species to generate the highly reactive hydroxyl radical, represents a system of exceedingly high reactivity.

SUMMARY OF THE INVENTION

It is a principal object of the present invention to provide rapid and effective decontamination procedures and apparatus for chemical and biological agents.

Another object of the present invention is to provide portable systems and methods for using same which utilize a gas-phase decontamination procedure.

Yet another object of the present invention is to provide a method and apparatus for decontaminating chemical and biological agents which is portable and uses highly energetic and reactive hydroxyl radicals in a gas system which can be used effectively to decontaminate both chemical and biological agents present in a variety of situations.

These and other objects of the present invention consist of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

DESCRIPTION OF PREFERRED EMBODIMENT

This invention capitalizes on the highly energetic and reactive properties of both the single atomic oxygen and hydroxyl radical species for the rapid and efficient decontamination of both chemical and biological agents. The application of the two reactive oxygen species $O(^1D)$ and OH toward both neat chemical agents and their simulants, has been the subject of earlier studies, which clearly demonstrated the feasibility of this approach. The prior art also suggests that this technique may be equally applicable for the decontamination of biological agents as well.

Figure 1:
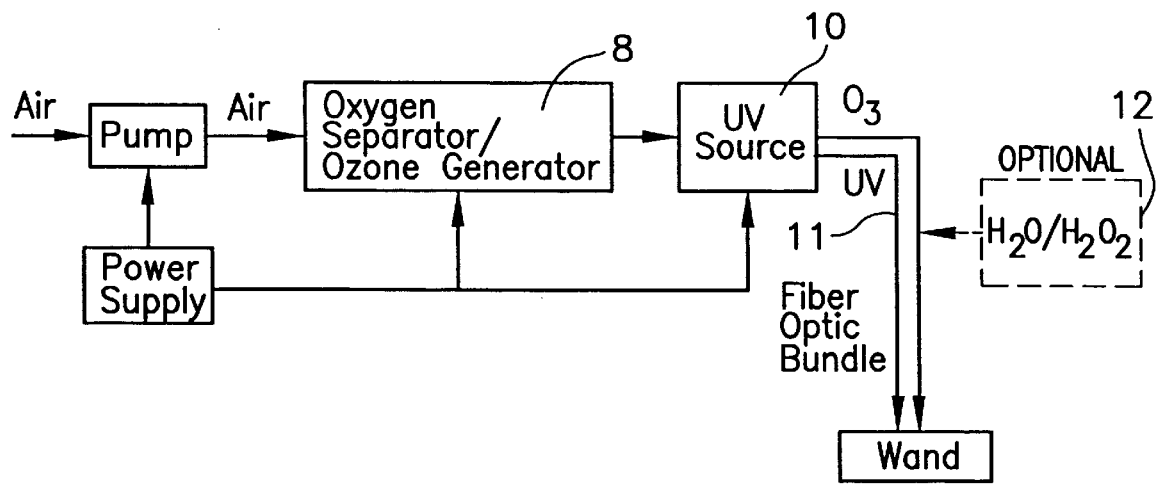
FIG. 1 is a schematic diagram of the process used to generate active decontamination agents where the UV source is located with the main unit.
Figure 2:
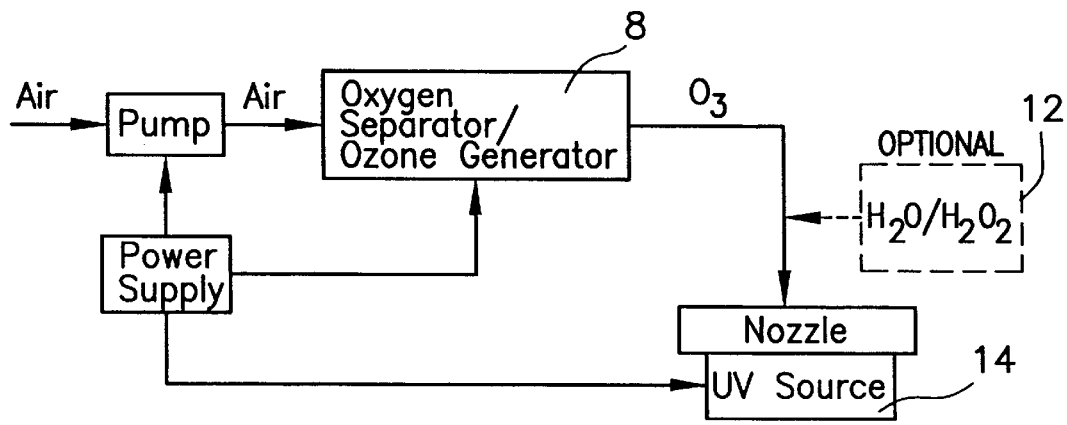
FIG. 2 is a schematic diagram of the process used to generate active decontamination agents where the UV source is located at the end of the wand.
Figure 3:
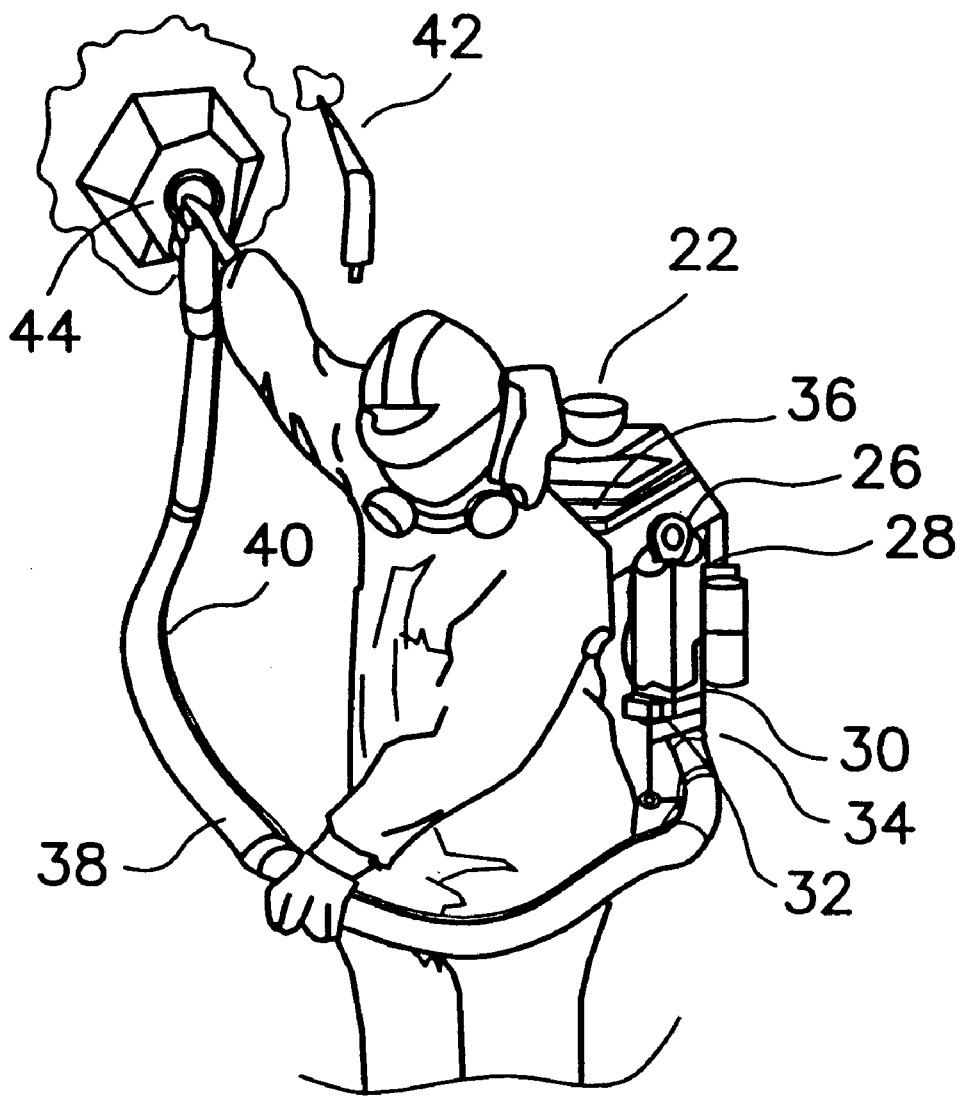
FIG. 3 is a line drawing illustration of a portable decontamination system.

The decontamination system of the subject invention works by generating a gas stream containing several highly reactive substances, which subsequently attack and destroy the target chemical or biological agent. These reactive species are extremely strong oxidizing agents consisting of both free hydroxyl radicals and singlet oxygen atoms that are generated through photolytically induced chemical reactions. FIG. 1, FIG. 2 and FIG. 3 illustrate schematically the proposed generation process and the apparatus used.

However, the apparatus as described would be suitable for use with other reactive reagents, in addition to the water and hydrogen peroxide reagents referenced herein.

This system utilizes a stream of oxygen or air in which ozone, $O_3$, has been produced using a standard ozone generator 8, FIG. 1 and FIG. 2. The ozone containing gas stream is then illuminated by intense UV light. Ozone is known to strongly absorb UV light. When ozone absorbs a photon having a wavelength between 315 and 1200 nm, it dissociates into an oxygen molecule and an oxygen atom in its ground ($^3P$) electronic state. In the presence of a large quantity of molecular oxygen, as would be the case if the ozone is produced in oxygen or air, the oxygen rapidly recombines to reform ozone, so that the net effect of the photolysis is the generation of a very low steady-state concentration of the $O(^3P)$ atoms:

$$O(^3P)+O_2+M\rightarrow+O_3+M$$

Here M is a third-body molecule ($O_2$ or $N_2$) required to remove excess energy in order to stabilize the ozone produced. If, however, the ozone molecule absorbs a photon in the UV range below 315 nm in wavelength, an electronically excited oxygen atom $O(^1D)$ is produced. The electronic transition between the excited $^1D$ and the ground $^3P$ state is forbidden by quantium-mechanical angular momentum conservation rules, and consequently the $^1D$ has a relatively long radiative lifetime of 110 seconds. In air at pressures close to one atmosphere, the most common fate of the $O(^1D)$ species is collisional deactivation to the ground state, from which ozone is again produced by recombination with an oxygen molecule.

$$O(^1D)+M\rightarrow O(^3P)+M$$

However, in the presence of water vapor, which is present in tenths of mole percent levels even in the driest desert air, a few percent of the $O(^1D)$ atoms will react to form two hydroxyl radicals as indicated below. This reaction is the main source of hydroxyl radicals in the Earth's atmosphere.

$$O(^1D)+H_2O\rightarrow 2HO$$

Hydroxyl radicals are extremely reactive and are believed to be the primary agents responsible for the removal of methane, carbon monoxide and other substances from the Earth's atmosphere, as well as playing an extremely important role in the generation of photochemical smog near the Earth's surface. Typical rural midday HO concentrations near the surface of are on the order of $5\times10^6$ molecules $cm^{-3}$, and typical reaction rates with gaseous organic molecules are on the order of $10^{-11}$ $cm^{-3}$ $molecule^{-1}$ $s^{-1}$. Consequently, the lifetime of a typical non-urban atmospheric organic species subject to attack by HO is on the order of $2\times10^4$ seconds, or about 5.5 hours.

Preliminary calculations indicate that it is possible to produce steady-state HO concentrations on the order of $10^{11}$ molecules $cm^{-3}$, 4 to 5 orders of magnitude higher than the typical value given above. This would lower the lifetime of a gaseous organic species to approximately one second. The lifetime of an organic species adsorbed onto a surface would be similar. Thus, the system proposed here is an excellent candidate for a photochemically-based gas-phase decontamination system for chemical and biological agents.

In FIG. 1, the ultraviolet source 10 is mounted in a backpack device 20, FIG. 3, or on a cart (not shown), and the UV light is transmitted to the nozzle via a fiber optic bundle 11, FIG. 1. This configuration allows the nozzle delivery line to be flexible and to have a cross-sectional area of similar size to that of a pencil thus, allowing the nozzle to penetrate and access the internal spaces and compartments of electronic instruments and equipment. In the alternative, a larger capacity delivery line can be used for surface area decontamination. In the second configuration, FIG. 2, the ultraviolet source 14 is located directly in the nozzle where it can provide for broad surface decontamination through the formation of OH radicals. In both cases, the concentration of the hydroxyl radical can be increased through the optional injection of water and/or hydrogen peroxide into the gas stream as is shown in FIG. 1 and FIG. 2, by source 12; thus, increasing the decontamination capability of the system. In addition to the afore described embodiment, the apparatus would also be suitable for use with other reactive agents for use in the decontamination of chemical and biological agents. In addition, although the instrument is configured with its own UV source, the UV light used for ozone photolysis can also be supplied by an external UV source which can illuminate the field in which the singlet atomic species are delivered, thus, producing the same decontamination capability as if the UV light were supplied by the instrument.

The process begins with a stream of air, oxygen enriched air, or oxygen to produce ozone using a suitable ozone generator. For the case as shown in FIG. 1, the gas stream is then passed into a tube in which it is exposed to ultraviolet light with the proper spectral range to photolytically break down the ozone into molecular oxygen and oxygen atoms, while the UV light is transmitted to the substrate using fiber optic bundles. A few percent of the oxygen atom produced are in the first excited electronic state $O(^1D)$, while the rest are at the ground state $O(^3P)$. The ground state oxygen atoms rapidly recombine with molecular oxygen to reform ozone, and most of the $O(^1D)$ atoms are returned to the ground state via collisional deactivation. However, $O(^1D)$ is a highly reactive species and will react with any water vapor present to produce two hydroxyl radicals (OH). Subsequent chemical reactions result in the additional formation of hydroperoxy radical ($HO_2$) and hydrogen peroxide ($H_2O_2$). Hydrogen peroxide itself, when introduced into the gas stream will, as is shown in the optional cases 12 in FIG. 1 and FIG. 2, photolyze under UV light. The incoming gas composition, flow rate, and other factors are manipulated to optimize the process output for different types of decontamination requirements. Preliminary calculations indicate that gaseous concentrations of $HO_2$, OH, and $O(^3P)$ of 1000, 29, and 3 parts-per-billion (by volume), respectively, should be attainable.

The gas stream, containing the above reactive species, is then directed onto a surface to be decontamination which optionally can also be illuminated with UV light, either with a direct UV source 14 or by using fiber optics and a source 10 located remotely from the nozzle. This configuration maintains the highest abundance of these reactive species at the point of decontamination. Alternatively, if available, the substrate surface can be illuminated with UV light from an external source, in order to enhance the formation of the reactive species. These energetic species are all highly reactive toward most organic substances and, in fact, represent some of the most powerful oxidants known. Chemical warfare agents that contain hydrogen and biological agents are readily susceptible to attack by these species and are rapidly degraded. Prior experiments with a mustard simulant (thiodiglycol) indicated a half-life of seven seconds. Testing on other chemical agents and biological simulants also produced very promising results.

A realistic final design and configuration of this decontamination apparatus is a hand-carried, cart carried, or a portable back-packed-type unit that can be readily transported into remote or isolated locations, if necessary. FIG. 3 is a representation of the backpack type unit the other units would have the same components only arranged and transported differently. Since the unit is a gas phase decontamination system, it is particularly applicable to electronic components and equipment. In the present design, the decontamination unit is in two basic parts. Part No. 1, the portable, "back-pack" portion of the unit, contains; an air intake 22, a small air pump 26 to supply the ambient air to the system, a hollow fiber membrane separator 28 to enrich the oxygen content of the gas stream, an ozone generator 30, a UV source 32, a water or hydrogen peroxide (reagent gas) reservoir 34, and a battery operated power supply 36. The backpack component of the system delivers an oxygen/ozone enriched gas supply through a photolysis cell to the entrance of a hand held delivery line, approximately 1–2 inches in diameter 38, smaller diameters are also possible. Part No. 2 of the system consists of a "snorkel-type" delivery line, which contains quartz fiber optic bundles 40 to transport UV light throughout the length of the delivery line to the nozzle and onto the substrate. The $O_2/O_3$ gas supply is delivered to the nozzle end of the snorkel through the annular space between the fiber optic bundles of the delivery line. This design enhances UV photolysis and hence the optimal production of the various reactive and energetic oxygen species. As described above, these reactive oxygen species will, in turn, generate hydroxyl radicals from water vapor or hydrogen peroxide introduced into the gas supply at the entrance to the delivery line or obtained from ambient air surrounding the nozzle 42. It is expected that the ambient water vapor in the original inlet air supply, which will be present in the exhaust stream of the membrane separator, will be reintroduced into the delivery line at the nozzle to facilitate the delivery of the oxidant species. In situations where water and/or hydrogen peroxide are available, these reagents are preferably incorporated into the delivery system to increase the effectiveness and efficiency of the system.

As an alternative to the above configuration, the UV light source 44 can be mounted at the nozzle 42 end of the snorkel assembly, thereby eliminating the need for the quartz fiber optic bundles and, accordingly, eliminate the energy losses associated with the delivery of the UV light through the quartz fibers. In addition, the backpack UV source 32 can be eliminated. This second configuration has the advantage of generating the reactive species directly at the surface of the substrate, optimizing the decontamination process. The surface to be decontaminated will be continually bathed in UV light (internal or external source) while ozone is flowing over the substrate surface. The OH radicals produced will be proportional to the area the UV light illuminates and the delivery line ozone concentration, while not limited to a fixed distance from the nozzle orifice. In addition, if the unit is employed in a fixed location, it is possible to deliver enriched oxygen to the ozonator, thus bypassing the membrane separator. Adequate panel mounting connectors are placed on the unit to accommodate such alternate configurations. Such connectors would also include electrical adapters for direct line operation when available, and for recharging the battery pack.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical applications and should enable others skilled in the art to utilize the invention in various embodiments and with various modifications as are suited to the particular use contemplated. It is intended that the scope of the invention be defined by the claims appended hereto.

The embodiment of this invention in which an exclusive property or privilege is claimed is defined as follows:

1. An apparatus for gas phase decontamination of dangerous chemical and/or biological agents comprising:
   a pump for introducing an initial stream of air to an initial gas line;
   a means for controlling a rate at which said air enters said decontamination apparatus;
   an ozone generator where said ozone generator is coupled to said initial gas line where a modified gas departs said ozone generator via a secondary gas line and wherein a hollow fiber membrane separator for enriching the oxygen content of said air stream is coupled into said initial gas line upstream from said ozone generator;
   an ultraviolet source positioned downstream from said ozone generator and oriented in such a manner that when said ultraviolet source is activated, said modified gas stream leaving said ozone generator is subjected to ultraviolet radiation from said ultraviolet source and where an irradiated gas leaves said ultraviolet source via a tertiary gas line;
   a gas delivery tube coupled to said tertiary gas line at a first end and coupled to a nozzle at a second end;
   a fiber optics bundle which optically links said ultraviolet source a nozzle tip for irradiating said gas in said nozzle;
   a source of water vapor and/or hydrogen peroxide which is connected to said nozzle to add water vapor and/or hydrogen peroxide to a gas passing through said tertiary line and where an exhaust tube from said membrane separator is coupled to said nozzle to combine water vapor from the exhaust gas with said gas in said nozzle;
   a power source electrically coupled to those components requiring electrical power.

2. The apparatus of claim 1 wherein said initial air stream is replaced by an oxygen stream.

3. The apparatus of claim 1 wherein said initial air stream is replaced by an oxygen enriched air stream.

4. A method for decontaminating hazardous biological and chemical agents comprising:
   drawing either air or oxygen containing oxygen into a decontamination system at a controlled rate;
   flowing said gas through a membrane separator to enrich the oxygen content of said gas;
   removing an exhaust gas from said separator piping said gas from said membrane separator to an ozone generator to convert some of said oxygen in said gas to ozone;
   subjecting said gas which exits from said ozone generator to ultraviolet radiation in a spectral range to photolytically break down said ozone in said gas stream to molecular oxygen and oxygen atoms;
   transporting said gas to a delivery tube having a nozzle and injecting some of said exhaust gas containing water vapor from said stream leaving said separator to said gas delivery tube at said nozzle via an inner connecting tube;
   employing a fiber optic cable to transmit ultraviolet light from a ultraviolet source to the nozzle;

subjecting said gas in the nozzle to ultraviolet radiation from said ultraviolet source;

applying the nozzle to an area to be decontaminated and allowing said gas exiting said nozzle to interact with said area to be decontaminated.

5. The method of claim 4 wherein water vapor and/or hydrogen peroxide are added to said gas through a port to a delivery tube.

6. The method of claim 4 wherein a flow rate is controlled to provide optimum performance depending on the type decontamination requirements.

7. A method for decontaminating biological and chemical agents comprising:

drawing a gas containing oxygen into a decontamination system at a controlled rate;

flowing said gas through a membrane separator to enrich the oxygen content of said gas;

removing an exhaust gas from said separator;

piping said gas from said membrane separator to an ozone generator to convert some of said oxygen in said gas to ozone;

transporting said gas to a delivery tube having a nozzle and bleeding some gas containing water vapor from said gas stream leaving said separator to a connecting tube which is in fluid contact with a port in said delivery tube at said nozzle;

subjecting said gas in the nozzle to ultraviolet radiation from an ultraviolet source located in conjunction with said nozzle where said ultraviolet radiation has a spectral range to photolytically break down said ozone in said gas stream to molecular oxygen and oxygen atoms;

applying the nozzle to an area to be decontaminated and allowing said gas exiting said nozzle to interact with said area to be decontaminated.

8. The method of claim 7 wherein water vapor and/or hydrogen peroxide are added to said gas through a port to a delivery tube.

9. The method of claim 7 wherein a flow rate is controlled to provide optimum performance depending on the type decontamination requirements.

* * * * *